United States Patent [19]
Rink

[11] Patent Number: 5,092,865
[45] Date of Patent: Mar. 3, 1992

[54] OPTICAL FIBER FAULT DETECTOR

[75] Inventor: John L. Rink, San Francisco, Calif.

[73] Assignee: Xintec Corporation, Oakland, Calif.

[21] Appl. No.: 569,984

[22] Filed: Aug. 20, 1990

Related U.S. Application Data

[63] Continuation of Ser. No. 265,565, Nov. 1, 1988, Pat. No. 4,950,268, which is a continuation-in-part of Ser. No. 19,755, Feb. 27, 1987.

[51] Int. Cl.$^5$ .............................................. A61B 5/06
[52] U.S. Cl. ...................................... 606/12; 606/10; 606/15; 606/16; 128/395; 128/398
[58] Field of Search ..................... 606/10–19, 606/26–28; 128/395, 397, 398

[56] References Cited

U.S. PATENT DOCUMENTS 4,662,368  5/1987  Hussein et al. ........................ 606/28

FOREIGN PATENT DOCUMENTS

212786  3/1987  European Pat. Off. .............. 606/12

*Primary Examiner*—David Shay
*Attorney, Agent, or Firm*—Howard Cohen

[57] ABSTRACT

A control apparatus for a pumped rod-type laser includes an arc lamp disposed to illuminate the lasing medium, such as a NdYAG crystalline rod. The apparatus includes a full wave rectifier to power the arc lamp, and a MOSFET switching circuit to turn on and off the arc lamp power at controlled times during each half cycle of the power waveform so that the laser medium is pumped and optically discharged once during each half cycle of the power supply. The laser power output is measured by a photodetector during each half cycle, and the photodetector output is integrated and compared with a manually set, variable laser output power level. When the actual laser power reaches the preset power level, the comparator initiates turning off the MOSFET switching circuit power for that respective half cycle of the power waveform. The apparatus also includes safety circuits that permit laser operation only when the internal cooling system is operating, when the current to the arc lamp is below a maximum level, and when the temperature created by the laser illumination on a target is below a variable preset level, and the like. A further safety circuit detects the presence of laser radiation in the area surrounding the laser to shut it off when laser light escapes from the system. For medical uses, this feature obviates the need for laser safety goggles for operational personnel.

7 Claims, 9 Drawing Sheets

Figure_1

Figure_2

Figure_3

Figure_4

Figure_5

Figure_7

Figure_8

Figure_9

OPTICAL FIBER FAULT DETECTOR

REFERENCE TO RELATED APPLICATION

This application is a continuation of U.S. patent application Ser. No. 07/265,565, filed Nov. 1, 1988, now U.S. Pat. No. 4,950,268, issued Aug. 21, 1990, which is a continuation-in-part of U.S. patent application Ser. No. 07/019,755, filed Feb. 27, 1987 by the present inventor and Dan Rink and Garrett Lee, for which priority is claimed.

BACKGROUND OF THE INVENTION

In the field of medicine the use of laser devices for treatment purposes is becoming commonplace. Such devices are used for cauterization of wounds, excision of tissue, selective thermal absorption in tissue, welding of tissue through the formation of scar tissue, and the like. Recent developments in intravascular treatment point to recanalization of atherosclerotically occluded vessels virtually anywhere in the human body, including the relatively small vessels which supply the heart muscle itself. Such developments are described in co-pending U.S. patent application Ser. No. 07/109,755, filed Feb. 27, 1987 by the present inventor and Dan Rink and Garrett Lee.

Generally speaking, lasers designed for medical use should be highly controllable with respect to the power output level of the laser, and the duration of the laser illumination. Paradoxically, although the laser output power rarely exceeds approximately 20-25 watts for medical treatment purposes, the amount of power used to generate this laser power level is extraordinarily high. In lasing medium which operates continuously, kilowatts of power are consumed, even on a standby basis, so that a few watts of light energy can be delivered briefly or sporadically to the desired application site. The heat generated in the lasing cavity and in the power supply require that an external cooling system be provided. Thus an external source of cold water is generally required, and hundreds of gallons of water are expended in relatively short procedures. External cooling systems add to the complexity and expense of a medical laser, and create further connection and maintenance problems.

In pulsed mode laser devices, there is the opportunity to save power consumption since the lasing medium is operated only sporadically. However, pulsed mediums do not react predictably when first activated, due to thermal and dimensional effects. For example, when a NdYAG laser rod is first pumped by an arc lamp, the rod experiences a rapid thermal buildup which alters the axial dimension of the rod. As the rod changes in shape, the quality of the laser output pulse is severely affected. Thus prior art devices may provide erratic power outputs in pulse or burst modes of operation.

This problem is complicated by the fact that many prior art pulsed laser systems measure the power output of each pulse (by any of several techniques known in the art), compare that power level to a preselected level, and in response alter the intensity or period of succeeding pulses. The inherent time lag of this process, together with the averaging errors and the potential instability in such level-hunting systems, can create unacceptably erratic performance.

Prior art lasers have employed high voltage DC power supplies to pump and fire a pulsed mode laser, and pseudo-continuous operation may be added by charging capacitors with the high-voltage power and sequentially connecting the capacitors to a flash lamp or the like to fire the laser to produce a plurality of time-separated pulses. However, such power supplies are expensive and inefficient, and there is a limit to how many capacitors can be provided in a practical laser apparatus.

Another difficulty found in medical and other forms of work with lasers is that prudent safety considerations that all personnel wear laser safety goggles whenever they are in an area in which a laser is in use. Particularly in medical settings such as a surgical operating room, the surgeons and assisting staff, the anesthesiologists and the patient must be equipped with safety goggles. Often the goggles interfere with other equipment, such as sterile masks, the anesthesia mask, and the like, and are a distraction at best. There is no remedy for this problem known to the present inventors.

SUMMARY OF THE PRESENT INVENTION

The present invention generally comprises a laser driving method and system that provides a laser system with a high safety factor, low power consumption, and a compact, simplified power supply. The laser system includes a pumped rod-type laser and an arc lamp or the like disposed to illuminate the lasing medium, such as a NdYAG crystalline rod. The apparatus includes a full wave rectifier to power the arc lamp, and a MOSFET switching circuit to turn on and off the arc lamp power at controlled times during each half cycle of the power waveform so that the laser medium is pumped and optically discharged once during each half cycle of the power supply.

In order to control the power of the laser pulse, the laser power output is measured by a photodetector during each half cycle, and the photodetector output is integrated and compared with a pre-set, variable laser output power level. When the actual laser power reaches the preset power level, the comparator initiates turning off the MOSFET switching circuit power for that respective half cycle of the power waveform. At the beginning of the next half cycle the integrator is reset and the MOSFET switching circuit is turned on again. Thus the power of each pulse of the laser is measured and chopped at the appropriate instant to deliver the precise power level desired.

The full wave rectified power is used to drive the laser medium in a burst mode of several pulses, or in a repetitive pulsed mode that emulate the effects of continuous output lasers. The full wave rectified power supply also permits the use of 110 VAC utility power, and obviates the need for external cooling of the laser. The apparatus also includes safety circuits that permit laser operation only when the internal cooling system is operating, when the current to the arc lamp is below a maximum level, and when the temperature created by the laser illumination on a target or on a portion of the beam delivery system is above a variable preset level, and the like. A further safety circuit detects the presence of laser radiation in the area surrounding the laser to shut it off when laser light escapes from the system. For medical, industrial, and experimental laser uses, this feature obviates the need for laser safety goggles for operational personnel.

DESCRIPTION OF THE PREFERRED EMBODIMENT

The present invention generally comprises a laser driving and control system and method of operation thereof. The most salient features of the invention is that it provides a laser system which is power efficient, stable, accurately controlled and extremely safe. Although the preferred embodiment is described with respect to medical applications, it may be appreciated that the attributes of the laser system of the present invention could be directed to industrial, investigative, and other uses.

The invention is adapted to be employed with a standard-in-the-art laser generating unit, or head, which comprises a closed reflective chamber housing a lasing rod and an optical pumping source such as a flashlamp in operational relationship. One possible configuration of the laser head includes a optical enclosure having a uniform, elliptical cross-sectional configuration along a longitudinal axis, with focal lines parallel to the longitudinal axis, and the laser rod and flashlamp extending parallel along respective focal lines. The lasing rod material may be NdYAG or the equivalent. A conventional cooling system which circulates coolant in the laser head is provided to remove excess heat generated by absorption of a good portion of the flashlamp energy by the laser head.

A significant aspect of the invention is the design and operation of the power supply that controls the flashlamp and thus the laser output power level. Unlike prior art laser systems, which use high voltage DC power supply arrangements, the present invention is designed to use 117 VAC (or 110 VAC) power directly from the utility power source. With regard to FIG. 1, the power control circuit includes a transformer 11 to step down the input line voltage and deliver it to a full wave rectifier 12. The result is the rectified sinusoidal power wave P, shown in FIG. 6. The power wave P is fed to a Zener diode voltage regulator, which chops the peaks of the power wave P at a desirable voltage to form a low voltage analog of the power voltage signal.

Figure 1:
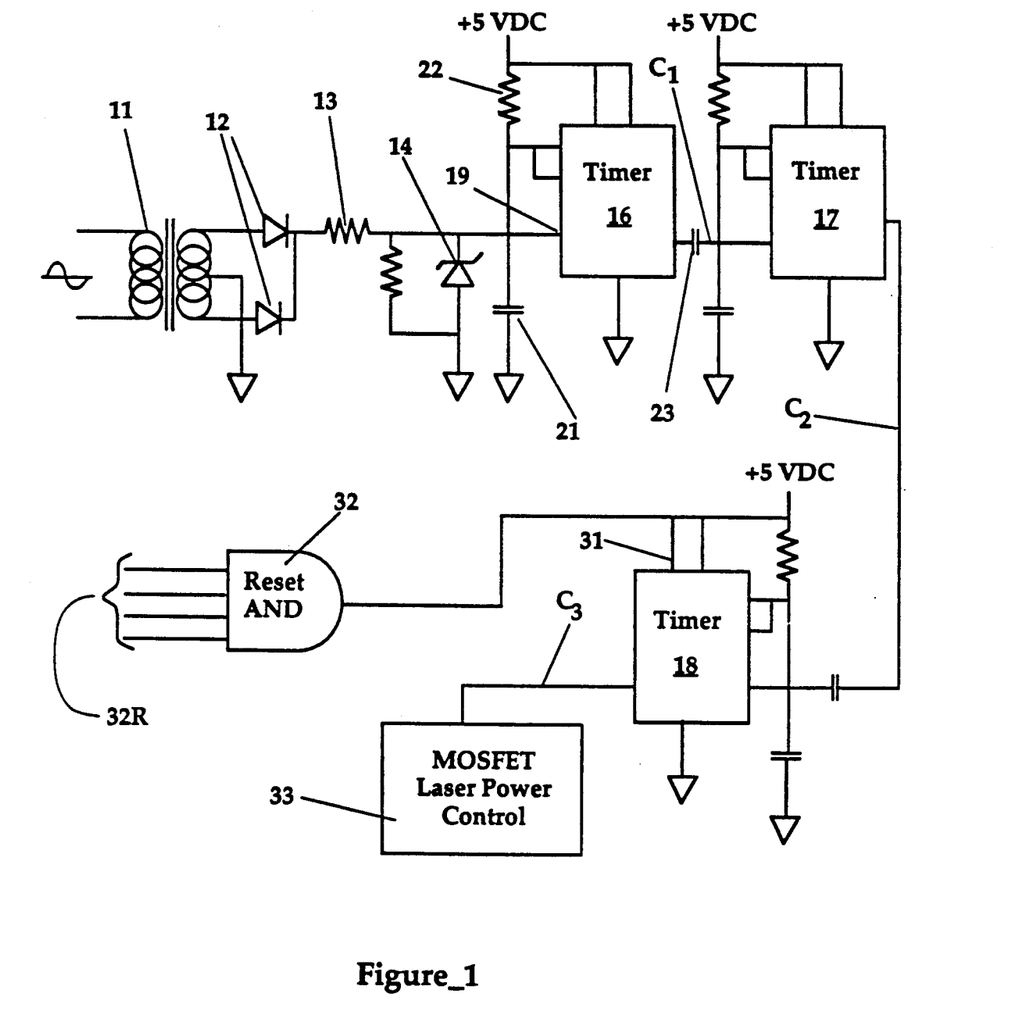
FIG. 1 is a schematic representation of the laser power control circuit of the present invention, and in particular the circuit that senses and controls the portion of each half cycle of the power waveform that is applied to the laser pumping light source.

The analog power signal is fed to the trigger input of a timer 16, such as the common 7555 IC timer known in the prior art. The circuit includes a trio of such timer circuits 16, 17, and 18, connected output-to-input in serial fashion. The input 19 of timer 16 is connected between a capacitor 21 leading to ground, and a resistor 22 connected to the 5 VDC power supply which also drives the timer 16. As is known in the prior art, the resistor 22 and capacitor 21 comprise an RC network which slowly charges the input 19 to 5 volts in a time period determined by the values of the resistor and capacitor. Each of the timer circuit 17 and 18 operate in a similar fashion, although the values of the respective resistors and capacitors at the input differ to determine selected time delay factors.

In addition, the power wave analog signal is connected to the input 19. Whenever this signal pulls the input low, to a range of one-third the power supply voltage, the timer output 23 goes high forming the signal $C_1$ depicted in FIG. 6. Note that signal $C_1$ switches high as the power waveform P approaches zero, and stays high until P exceeds the threshold voltage once again. The on-off thresholds may be set to be identical so that the signal $C_1$ is symmetrical about the zero point of the power voltage P, but this in not necessary for the system to operate.

The output of timer 16 is connected to the input of timer 17, which is connected to be triggered immediately by the fall of signal $C_1$ and to remain on only a short time. The output of timer 17, signal $C_2$ is fed to timer 18, which is connected to produce the signal $C_3$. It is important to note that signal $C_3$ commences when $C_2$ goes low, so that $C_2$ comprises a firing signal for the system. The output of timer 18 is connected to an actuating input of a MOSFET laser power supply control 33, described in the following specification, so that the laser pumping light source is turned on whenever signal $C_3$ goes high. The operating period (on time) of timer 18 also establishes a maximum elapsed time for operation of the pumping light source during each half cycle of the power voltage waveform.

It should be pointed out that the timer 18 differs from the others in that the reset input 31 is not connected to the 5 VDC power supply for instant reset. Rather, input 31 is connected to the output of reset AND gate 32, which has a plurality of reset inputs 32R. Whenever any of the reset inputs receive a low-going input, the AND gate 32 causes the timer 18 to reset and the output $C_3$ goes low. Thus the inputs to gate 32 determine that period of each pulse of signal $C_3$ and the laser pulse itself may be terminated before the maximum elapsed time, as shown by reference numeral $RC_3$ in FIG. 6. Furthermore, a continued low input to the gate 32 will effectively block operation of the laser. Thus the inputs 32R comprise important control factors for the operation of the laser.

Figure 4:
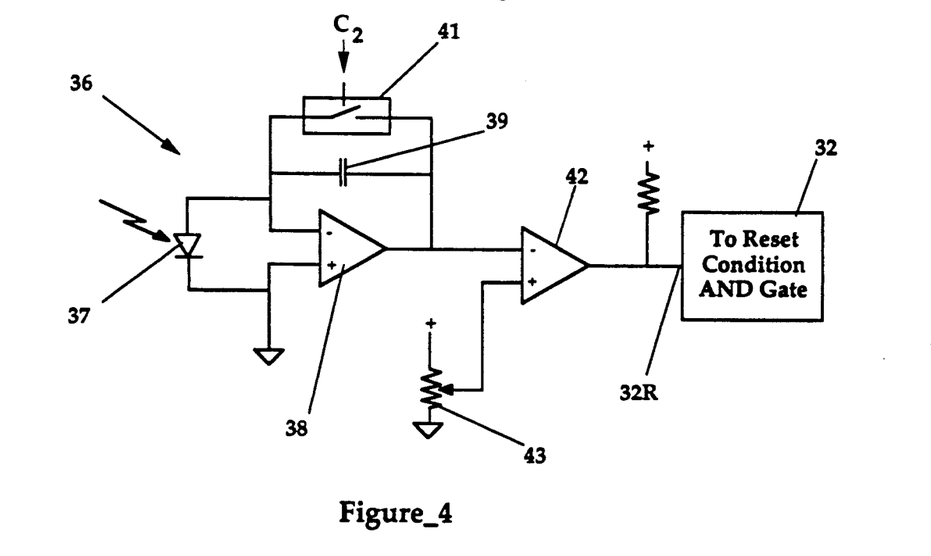
FIG. 4 is a schematic representation of a portion of the laser power control circuit of the present invention, and in particular the photodetector circuit that senses the laser output during each half cycle of the power waveform, and shuts off the laser whenever a desired, preset output power level is reached.

With regard to FIG. 4, another important portion of the invention is an output power monitor circuit 36, which has an output connected to one of the reset inputs 32R. The circuit 36 includes a photosensor 37, preferably a linear response photodiode fabricated of silicon or the equivalent, and placed in the laser light path to receive a small fraction of the laser output beam. For example, the photosensor 37 may be placed behind a partially conducting mirror disposed in the laser beam path, to receive the small percentage of beam power that is passed by the mirror. The photosensor outputs are connected across the inputs of an operational amplifier 38. The output of the op amp 38 is connected to the negative input in a feedback loop by capacitor 39, so that the output current of photosensor 37 is integrated with respect to time and represented by the voltage across the capacitor 39. The integration product is an analog signal having a voltage level which varies generally linearly with the energy output of each laser pulse.

Also connected in parallel with the capacitor 39 is a solid state switch 41. The switch 41 has a trigger input connected to receive the signal $C_2$ and is actuated thereby to short out the capacitor and remove the accumulated voltage thereon. Thus the firing signal $C_2$ resets to zero the voltage signal at the op amp 38 output just prior to firing the next laser pulse.

The voltage signal output of op amp 38 is conducted to the negative input of op amp 42. The other input is connected to the wiper connection of a potentiometer 43, which may be controlled manually or by appropriate software. It may be appreciated that whenever the signal from op amp 38 exceeds the voltage set by potentiometer 43, op amp 42 will emit a low-going signal that is connected directly to one of the inputs 32R of the reset AND gate 32. Thus the energy output of each pulse of the laser is monitored in real time, and the power supply is squelched when the pulse energy equals the selected, desirable pulse energy level. This system is extremely accurate in delivering the desired laser energy to the device utilizing the laser radiation, since it eliminates pulse power averaging errors and correctional time delays which are known in prior art systems.

Figure 3:
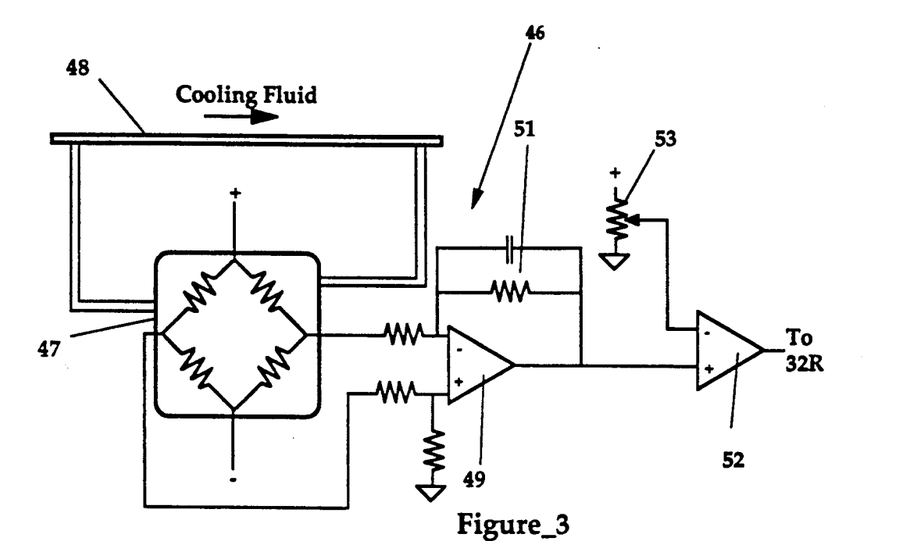
FIG. 3 is a schematic representation of a portion of the laser power control circuit of the present invention, and in particular the cooling safety circuit that shuts off the laser power supply whenever there occurs an interruption in flow of coolant to the laser cavity.

Another control circuit 46 connected to the safety reset switch 82, shown in FIG. 3, is designed to monitor the cooling fluid flow to the laser head, and to deactivate the laser when there is insufficient coolant flow. The circuit 46 includes a bridge-type resistive fluid pressure sensor 47. The sensor 47 is connected by fluid conduits in a parallel relationship to the main coolant supply conduit 48, so that the pressure drop produced by fluid flow resistance in the conduit 48 is presented to the sensor 47. The opposed bridge outputs of the sensor 47 are connected across the inputs of op amp 49. Connected from the output to the negative input of op amp 49 is a parallel resistive network 51 which establishes a feedback loop. The output of op amp 49 is connected to the positive input of op amp 52, and the respective negative input is connected to the wiper contact of a potentiometer 53. When the voltage level of the output signal of the op amp 49 falls below a level set by potentiometer 53, indicative of a decrease in the fluid pressure on sensor 47 and a loss of coolant flow, the output of op amp 52 goes low, and the system reset switch 82 is disabled to stop all power to the laser pumping light source. Thus the laser output is stopped immediately.

Figure 2:
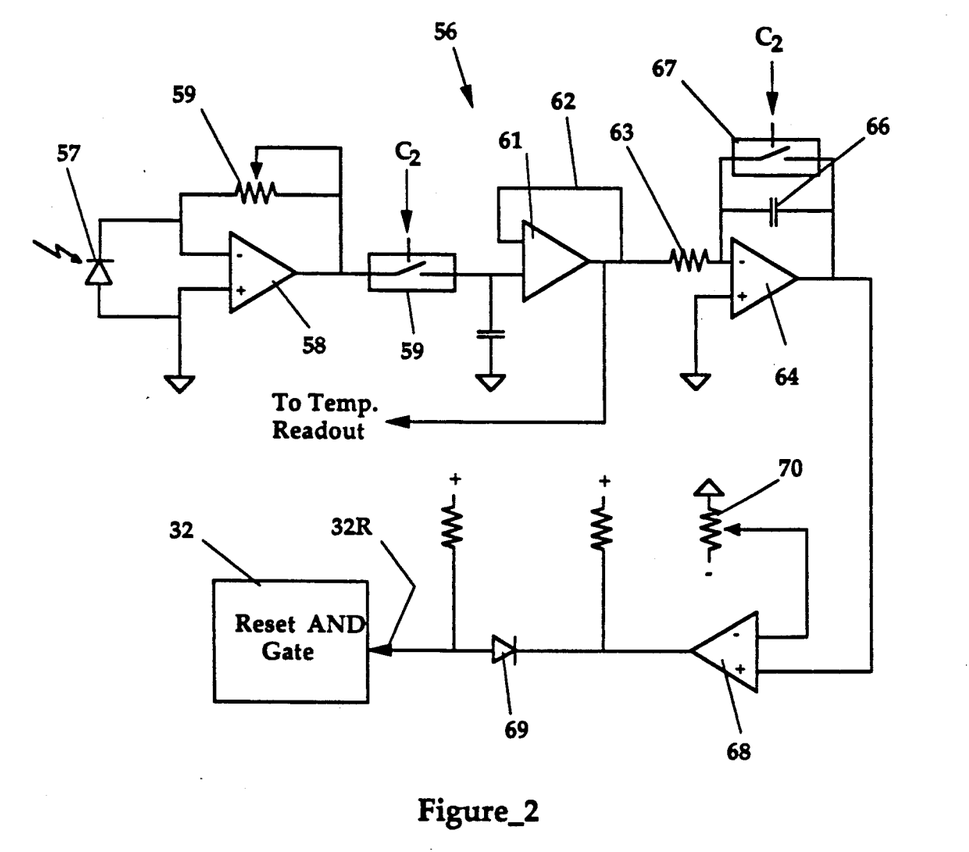
FIG. 2 is a schematic representation of a portion of the laser power control circuit of the present invention, and in particular the temperature safety circuit that senses an overtemperature condition in the laser system and shuts off power to the laser power supply.

A further safety circuit, shown in FIG. 2, is designed to prevent excessive heat in the laser system or in a laser beam receiving target from destroying system components by shutting off the laser when an excessive temperature condition is detected. The thermal safety circuit 56 includes an infrared sensitive photosensor 57, such as an infrared diode sensor, with its terminals connected across the inputs of an op amp 58. In a preferred embodiment of the invention, the infrared sensor may be directed to the transfer system that conducts the laser beam from the laser to a delivery system, such as fiberoptic beam guide that extends to a beam utilization device. An example of one such transfer system is described in copending U.S. patent application Ser. No. 07/180,950, filed on Apr. 11, 1988 by the present inventor, Dan Rink, and Garrett Lee, now U.S. Pat. No. 4,925,265, issued May 15 1990. The disclosure of that patent is incorporated herein by reference. In that apparatus there is a bushing component that supports the ends of a plurality of optical fibers while the focused laser beam is shifted among the plurality of fiber ends. Any misalignment of the focused beam can direct a focused laser pulse of extremely high power density onto the busing component, quickly generating very high temperatures that cause the emission of infrared light. The sensor 57 picks up the infrared light, and emits a proportional voltage in response thereto. Alternatively, the sensor 57 can be directed to monitor the infrared output of a beam-receiving target member, such as a laser heated cautery cap for recanalization of atherosclerotically occluded vessels, as described in the copending U.S. patent application Ser. No. 07/019,755, filed Feb. 27, 1987 and noted above.

The output of op amp 58 is connected to a solid state switch 59, which has a trigger input connected to the firing signal $C_2$. Switch 59 is connected in turn to the positive input of op amp 61, which is provided with a direct feedback loop 62 from output to input. The configuration of op amps 58 and 61 is such that the current level of the output of op amp 61 is proportional to the infrared radiation received by sensor 57. This current output signal is fed through resistor 63 to one input of op amp 64, so that the current through resistor 63 is a function of the magnitude of the infrared radiation. Op amp 64 includes a feedback capacitor 66 which integrates the current input to produce an output having a voltage proportional to the total infrared power received by the sensor, which in turn is indicative of the temperature of the component being sensed. Solid state switch 67 is connected in parallel with capacitor 66, and includes a trigger input connected to $C_2$. It should be noted that the firing signal $C_2$ causes the switch 67 to reset the integration product to zero prior to each laser pulse. Furthermore, the switch 59 connects the infrared signal to the integrator only during the brief firing signal, before the laser pulse is fired. This arrangement assures that the infrared source is monitored only when it is not being illuminated by the laser, which would overwhelm the infrared signal of interest.

The output of op amp 64, a voltage analog of the infrared power level and hence an indication of temperature level, is connected to one input of a comparator 68, and the output of comparator 68 is conducted through diode 69 to one of the reset inputs 32R. Comparator 68 includes a level-setting potentiometer 70 connected to the other input. Thus as the temperature of the monitored component increases, the voltage output of op amp 68 decreases, and when it fails to exceed the threshold of potentiometer 70 the output of op amp goes low and pulls the AND input 32R to a low state. This circuit effectively monitors the temperature of a component after a laser pulse, and serves to limit or chop the duration of the next successive laser pulse in response to the previous temperature level. For example, an excessive temperature condition in the component being monitored would cause the system to emit only a brief pulse in the next laser pulse cycle.

The present invention also includes a high voltage lamp driver circuit for operating the flashlamp or the like that optically pumps the laser rod to emit a coherent beam. With regard to FIG. 7, the lamp driver circuit includes a transformer 81 connected through a main shutoff relay switch 82 to 117 VAC utility power. The transformer 81 includes a high voltage secondary winding 83 having an output of approximately 600 volts that is connected across a full wave bridge rectifier 84. The rectified voltage is fed to a flashlamp current control circuit 86, which includes filter capacitors that produce a smooth DC current that in turn is connected to one electrode of a flashlamp 87. The other electrode of the flashlamp is connected to one output terminal of the rectifier 84. The circuit 86 applies approximately 160 VDC to the flashlamp to maintain the lamp plasma in a conductive state, emitting light at a level well below the threshold of lasing in the NdYAG rod. The current control circuit is also connected to a spark transformer 88, which has a high voltage output connected to a spark electrode 89 adjacent to the flashlamp 87. The spark transformer is activated by circuit 86 to provide a high voltage pulse to initiate flashlamp conduction, after which the circuit 86 provides a steady "simmer" current to maintain conduction in anticipation of a high current pulse to dramatically increase flashlamp output and initiate lasing.

Figure 7:
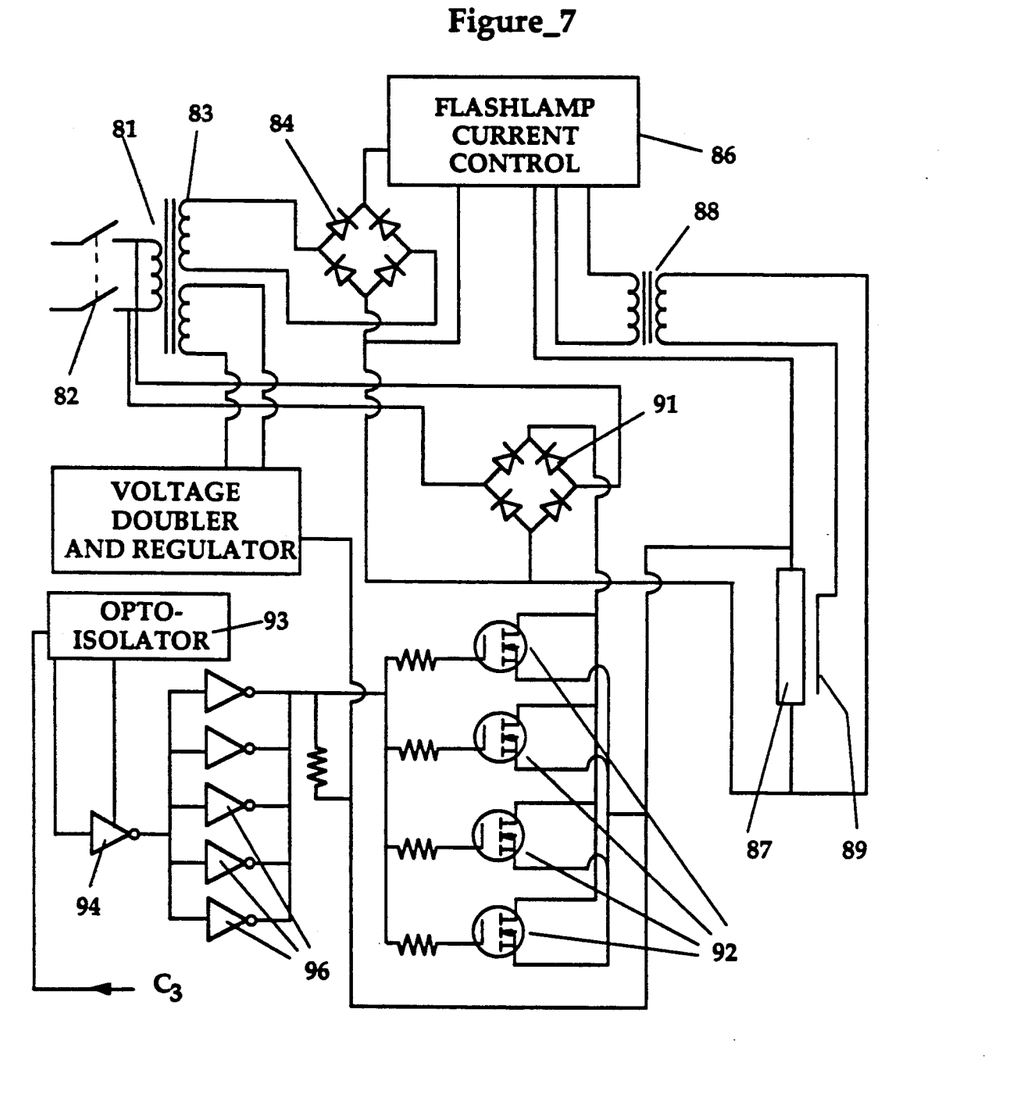
FIG. 7 is a schematic representation of a portion of the laser power control circuit of the present invention, and in particular the FET signal control circuit that delivers power to the laser optical pumping source.

To provide the high current pulse, the river circuit includes another full wave bridge rectifier 91 connected across the utility power supply. One output terminal of the rectifier 91 is connected to one electrode of the flashlamp, and the other output is connected to the drain terminals of a plurality of power MOSFETs 92 in a parallel configuration. The source connections of the MOSFETs 92 are connected in parallel fashion to the other flashlamp electrode. Thus switching of the MOSFET devices causes the output of the rectifier 91 to be applied directly across the flashlamp, and this branch of the circuit provides the substantial current required to sustain the output of the flashlamp at levels necessary to cause lasing.

Switching of the MOSFETs 92 is accomplished by signal $C_3$, which is fed to an opto-isolator 93 to isolate the logic circuits for the power circuits. The output of the isolator 93 is conducted to a two stage inverter, comprising gate 94 connected in series with a parallel array of gates 96. This double inverter arrangement comprises a high current source required to overcome the intrinsic gate-to-channel capacitance and switch the MOSFETs 92 as rapidly as possible. The outputs of gates 96 are connected together and lead to the gate connections of the MOSFETs 92. Thus whenever signal $C_3$ goes high, the MOSFETs 92 are switched on to provide high current to the flashlamp to sustain the lamp output as long as $C_3$ remains high. As soon as $C_3$ drops to zero, the MOSFETs switch off, lamp output ceases, and the maintenance voltage increases once again.

It may be appreciated that the control system of the present invention is closely tied to the utility power supply, not only in terms of voltage and current requirements, but also for timing control and repetition. Each half-cycle of the sinusoidal power wave provides a timing signal for the system, and the laser will fire repetitively, once each half cycle, as long as the system is turned on and none of the safety circuits are activated. Each pulse will have a maximum period set by the circuit of FIG. 1, and an actual period set by the laser power sensing circuit of FIG. 4.

Figure 5:
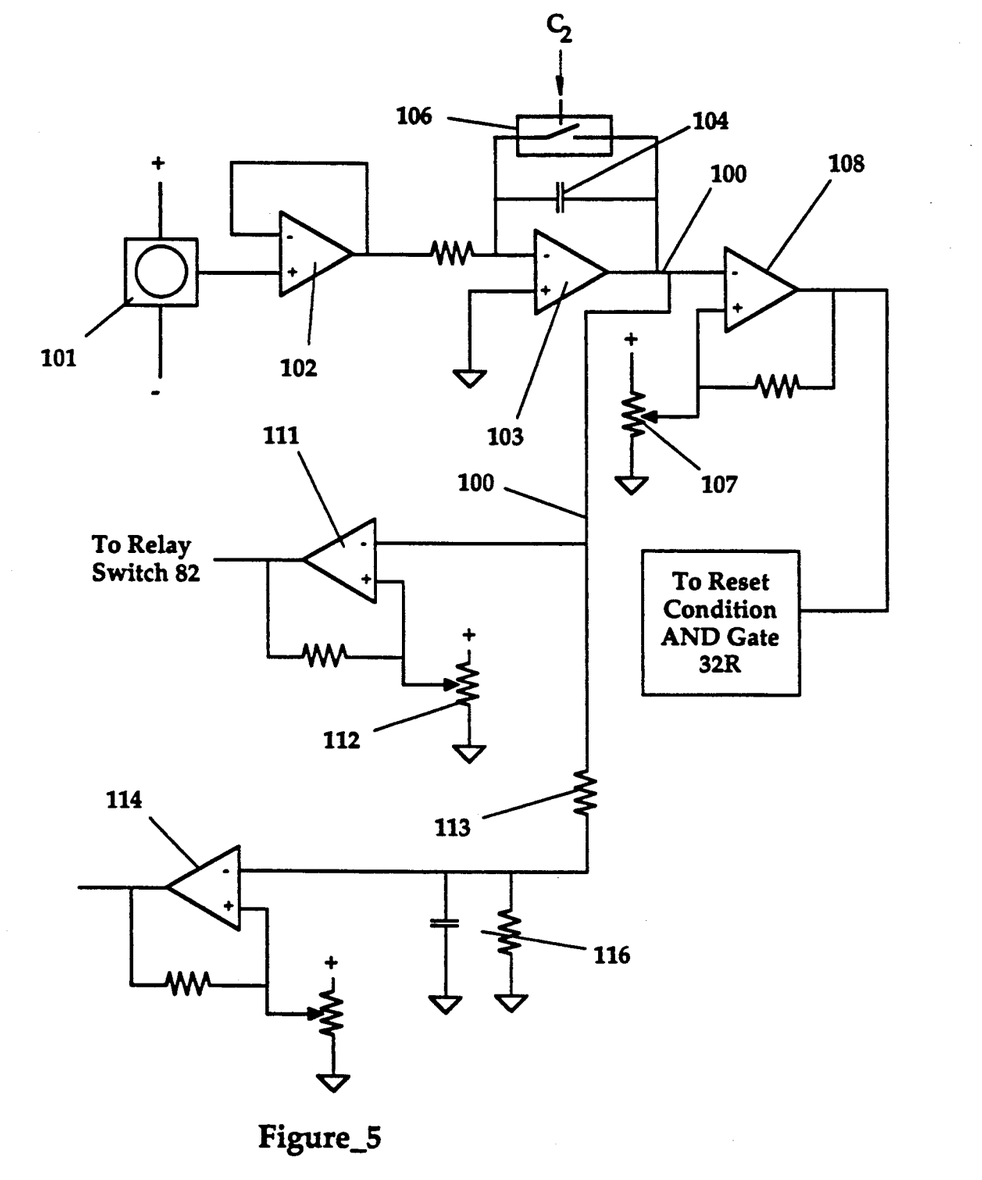
FIG. 5 is a schematic representation of a portion of the laser power control circuit of the present invention, and in particular the current level sensing safety circuit that detects excessive current flow in the conductor to the laser optical pumping source and shuts off the laser power system.

A further safety circuit, shown in FIG. 5, is designed to shut off the laser system when excessive current is detected in the power circuit feeding the flashlamp. It includes a Hall effect transducer 101 which is disposed about one of the conductors connected directly to the flashlamp and adapted to sense the magnitude of the magnetic field created by the current flow in the conductor. The output of transducer 101 is conducted to op amp 102, which in turn has an output connected through a resistor to the negative input of op amp 103. Op amp 103 is provided with a parallel combination of a capacitor 104 and solid state switch 106 connected between the output and negative input. The capacitor integrates the current generated by the transducer to produce a voltage signal output on signal line 100 proportional to the current flow to the flashlamp. The solid state switch 106, which is triggered by signal $C_2$ resets the integration product to zero prior to each laser pulse.

The output of op amp 103 is compared to an adjustable voltage reference 107 by comparator 108, the output of which is connected to one of the reset AND inputs 32R. Thus whenever the current to the lamp exceeds a selected maximum level, the laser is extinguished in the midst of an output pulse. The voltage produced by the potentiometer 107 sets the maximum current level permitted in the flashlamp driving circuit.

The voltage signal output on signal line 100, proportional to the current flow to the flashlamp, is also conducted to op amp 111, wherein it is compared with a further adjustable voltage reference 112. As before, the voltage level of reference 112 establishes a maximum current level sensing circuit. However, the output of op amp 111 is connected to the actuating input of relay switch 82, so that an excessive current condition in the flashlamp driver circuit will shut off power to the entire laser system. Thus not only is the laser pulse terminated by a high current condition (by op amp 108), but the entire laser control and driving system is disconnected from the utility power supply. This feature assures that any malfunction or short circuit will be neutralized immediately, no shock hazard will develop, and the system components will be protected.

The signal line 100 is further extended through resistor 113 to one input of op amp 114. This input is also connected to an RC integrating network 116, which produces a long-term average of the power consumed in the flashlamp driving circuit. This circuit detects current flow over the average of many laser pulses, and is provided as a further safety precaution to prevent excessive current flow.

Another salient feature of the present invention comprises a novel approach to safe use of a laser in medical or industrial settings. Generally speaking, it is necessary for all personnel to wear laser safety goggles which block light radiation in a narrow range of the laser output. These goggles comprise a large expense for a group of people, such as the operating team in a surgery. Furthermore, the goggles often are distracting and annoying, especially for individuals who wear eyeglasses.

Figure 8:
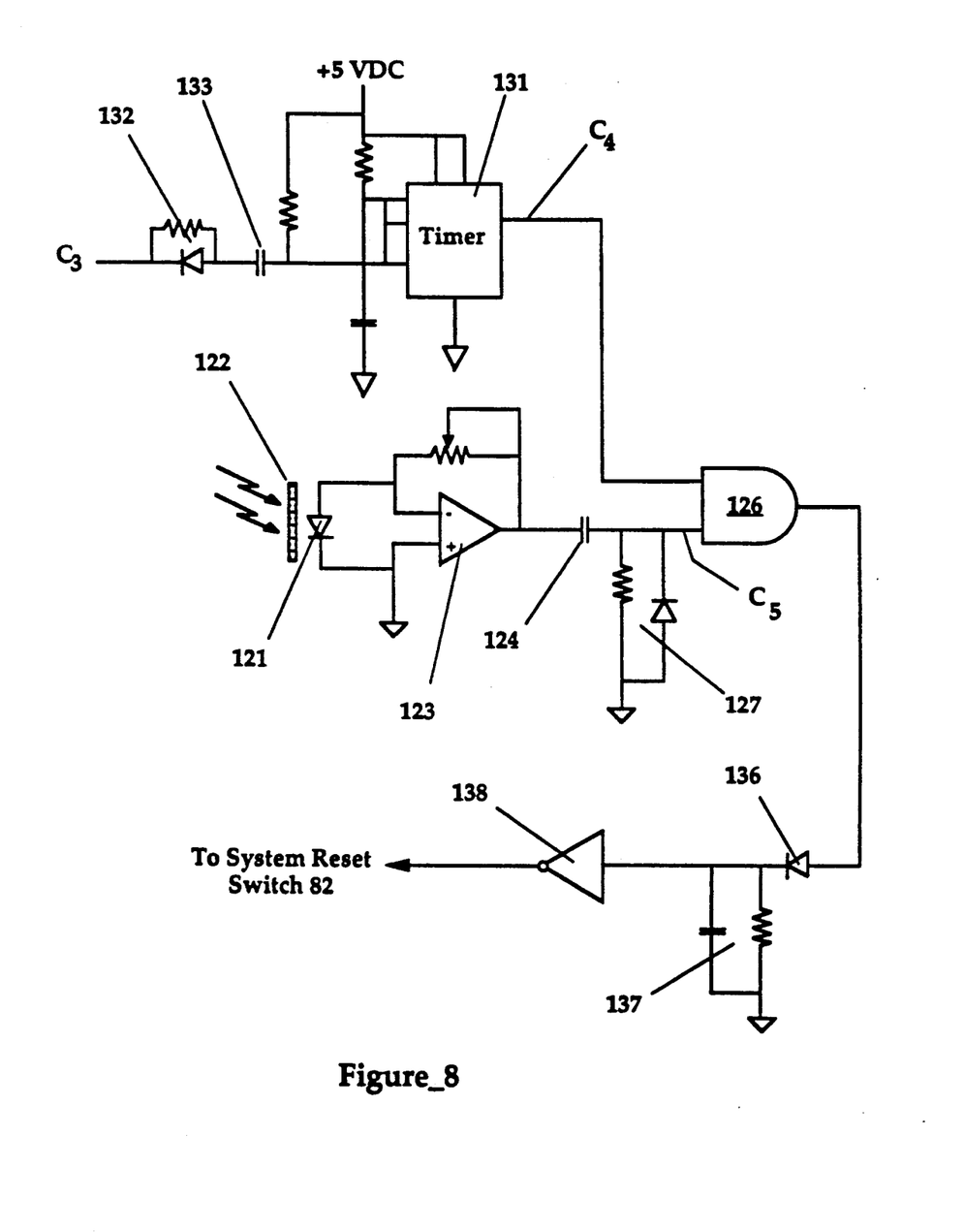
FIG. 8 is a schematic representation of a portion of the laser power control circuit of the present invention, and in particular the laser radiation area detector safety circuit.

In the present invention, these problems are alleviated by the provision of a further safety circuit shown in FIG. 8. This circuit, the laser radiation area detector, includes a photosensor 121 disposed adjacent to the housing in which the laser is enclosed, and directed obliquely toward a wall or ceiling surface in the room in which the laser is being used. The photosensor 121 may comprise a silicon photodiode or the equivalent, and is provided with a primary filter 122 that has a narrow optical passband in the range of the laser radiation. For example, commonly available filters transmit approximately 40% of light energy in the NdYAG output band, and only 1% of the remainder of the optical spectrum. The output of the photosensor, a current signal having a magnitude which is a function of the amount of laser light received by the sensor 121, is connected across the inputs of op amp 123. The output of op amp 123 is fed to differentiating capacitor 124, which in turn is connected to an input of AND gate 126.

Also connected to the same input is a parallel network comprised of a resistor and a diode extending to ground. The capacitor, in combination with this network, determines that a signal $C_5$ will appear on the input of gate 126 only when an abrupt negative change occurs in the amplitude of light in the narrow band of the laser output. (See also FIG. 6.) The component values are chosen so that the output signal $C_5$ will comprise a brief pulse, on the order of microseconds, in response to the photosensor 121 receiving a sudden negative change in the ambient light level in the laser output band. Since virtually any broadband light source will emit some light energy in the laser output band, and this output can vary, it is important to distinguish sudden negative changes in the output band level that are indicative of laser pulse energy escaping into the area surrounding the laser itself.

Figure 6:
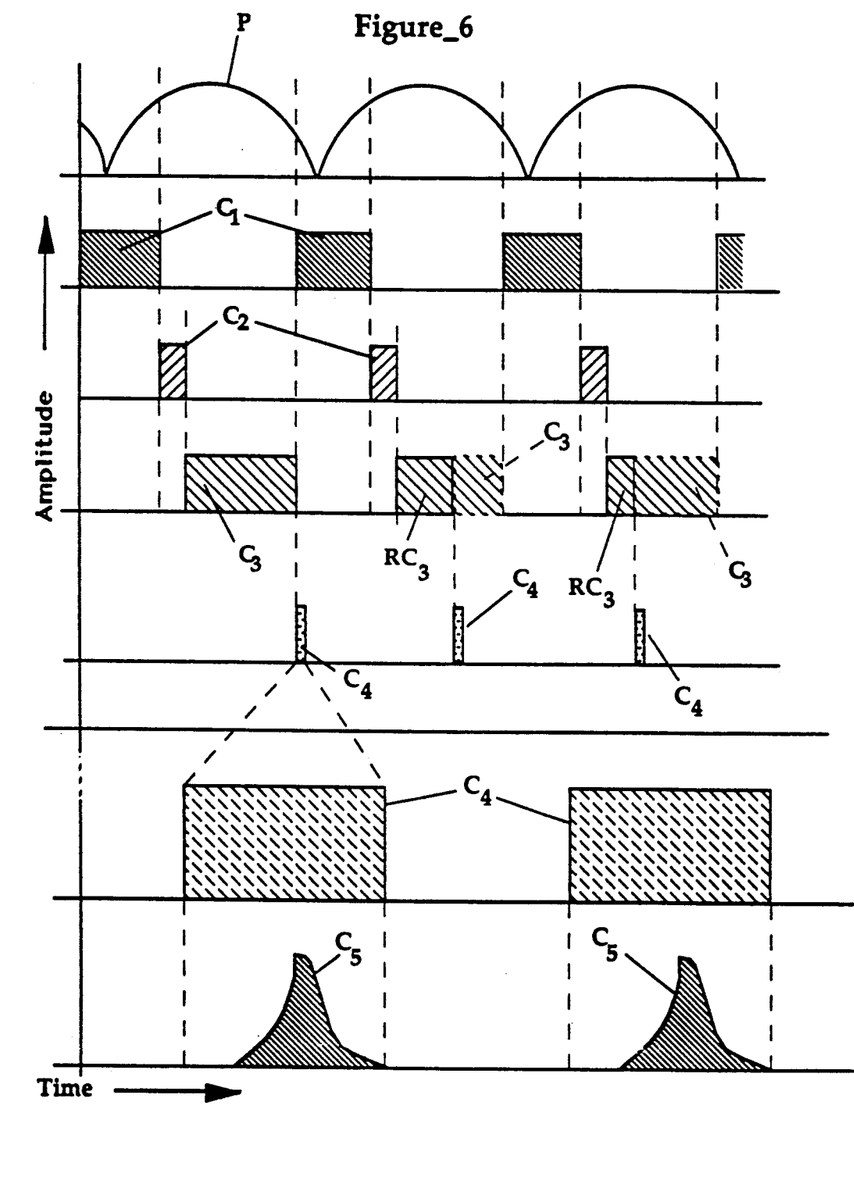
FIG. 6 is a graphic depiction of the timing sequence of the laser power control circuit of the present invention.

The laser radiation area detector also includes a timer 131, such as the standard 7555 timer known in the prior art, which is connected through resistor-diode network 132 and capacitor 133 to signal $C_3$. Timer 131 is configured to produce a short output pulse $C_4$, on the order of a few microseconds, immediately after signal $C_3$ (actually, RC3, since the signal is modified in duration by the various inputs to reset AND gate 32) goes to zero and the laser pulse has ended for that respective cycle, as shown in FIG. 6. Signal $C_4$, which effectively comprises a time window during which the ambient light signal is sampled and detected, is also input to the AND gate 126. When signals $C_4$ and $C_5$ are coincident in time, as shown in FIG. 6, AND gate 126 is actuated to produce an output signal during this signal convergence. Thus the gate 126 produces an output only when the photosensor 121 picks up an abruptly falling amplitude of area illumination in the laser output band, and only when this negative change occurs immediately after the cessation of a laser pumping, as the laser output is rapidly decreasing. Such convergence is a reliable indication of the escape of laser radiation into the area near the laser.

The output of gate 126 is fed through diode 136 to an integrating network 137 comprised of a resistor and diode connected in parallel to ground. It is also connected to an inverting gate 138 which has its output connected to the system reset switch 82. The integrating network 137 determines that more than one output pulse from AND gate 126 is required to trigger a signal from gate 138 to actuate switch 82 and shut off the laser system. In the preferred embodiment the component values are chosen so that two output pulses from gate 126 are required to shut off the laser system.

Due to the fact that the safety circuit of FIG. 8 reliably distinguishes laser radiation from background light and ambient light, including fluorescent lights, surgical lights, photographic flash lamps, sunlight, and the like, the use of laser safety goggles may be obviated.

The method of the present invention for controlling a laser is embodied in the functional description of the invention and in the operation of the various circuits described herein. The underlying concept in the method is the use of the AC power signal from the utility source, both as a power source and as a timing signal to drive a pulsed laser medium repetitively in synchronism with the AC power signal. The method of the present invention further includes the functional aspects of the laser safety circuits, for sensing temperature, power, and coolant flow, and in particular the laser radiation area detector that senses a decrease in area illumination in the laser output portion of the light spectrum in coincidence with termination of each laser pulse.

Figure 9:
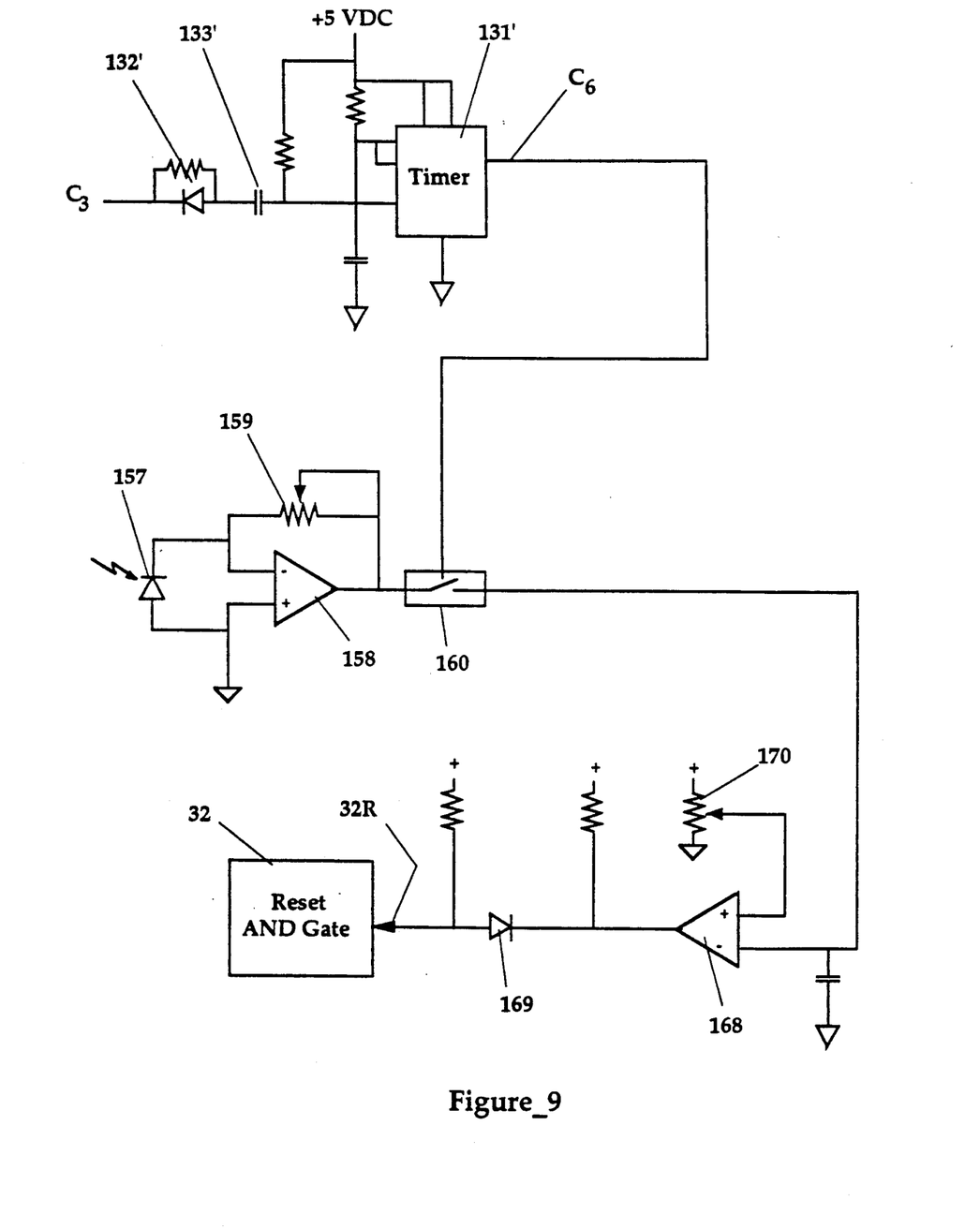
FIG. 9 is a schematic representation of the fiber break detector circuit of the present invention.
Figure 10:
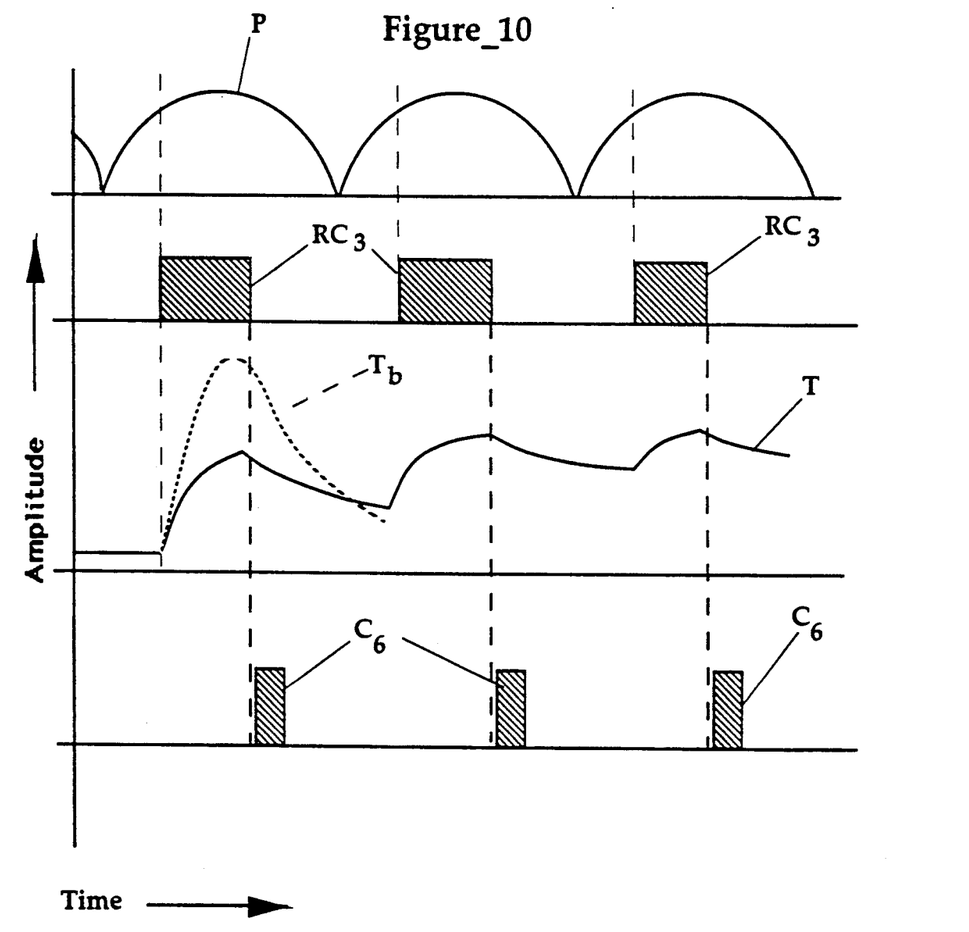
FIG. 10 is a graphic depiction of the timing sequence of the fiber break detector circuit of the present invention.

A further safety circuit of the present invention, depicted in FIG. 9, is designed to detect a break, fracture, or similar fault in an optical fiber delivery system connected to the output of the laser system. An optical fiber delivery system may be used to transmit the laser output to an intravascular cautery cap used for laser angioplasty, or a laser surgical too, or the like. As shown in FIG. 10, a plurality of laser pulses, occurring during control pulses $RC_3$, are used to heat an operating tip or tool element at the distal end of an optical fiber. The temperature of the operating tip, depicted by line T, tends to increase in stepwise fashion, with each laser pulse increasing the temperature and each quiescent period providing a small amount of cooling. Over the course of a few pulses the operating tip will heat to a nominal functioning range.

In contrast, a broken or fractured optical fiber exhibits a much different temperature characteristic. When an optical fiber breaks or fractures, some of the laser energy will radiate from that point, illuminating the adjacent jacket material of the fiber. The jacket material will rapidly heat to incandescence, as shown by line $T_b$ in FIG. 10, defining a temperature spike. Due to the low thermal mass of the jacket material, the incandescence will decay very rapidly after the laser beam is turned off. The black body radiation from the hot jacket material can be sampled just after a laser pulse finishes and before the jacket material cools significantly, and this radiation can be distinguished from the radiation from the heated tip of the surgical tool.

Returning to FIG. 9, the fiber break detector includes a timer circuit comprising a timer 131', such as a standard dual timer module known in the prior art, which is connected through resistor-diode network 132' and capacitor 133' to signal $C_3$. Timer 131' is configured to produce a short output pulse $C_6$, on the order of a few microseconds, shortly after signal $RC_3$ goes to zero (FIG. 10) and the laser pulse has ended for the respective cycle. The timer component values are selected so that the pulses $C_6$ are delayed sufficiently after the end of signal $RC_3$ to permit the laser pulse to extinguish, and to capture the timer interval in which incandescence of the fiber jacket would occur in the event of a break of fracture in the fiber.

The fiber break detector circuit includes an infrared sensitive photosensor 157, such as an infrared diode sensor, with its terminals connected across the inputs of an op amp 158. The infrared sensor is directed to receive infrared emissions from the optical fiber delivery system. The sensor 57 picks up the infrared light, and emits a proportional voltage in response thereto. The output of op amp 158, which is a temperature signal having a magnitude proportional to the temperature detected by the sensor 157, is connected to a solid state switch 160, which has a trigger input connected to the firing signal $C_6$. Thus the signal is conducted only during the brief period after the laser pulse is extinguished.

The temperature signal is conducted to one input of op amp 168, the other input being a voltage reference 170 that sets a threshold level. When the temperature signal exceeds the threshold level, the op amp 168 produces a signal that is conduced through blocking diode 169 to the reset gate 32R. Thus a temperature signal which exceeds an empirically determined threshold will cause the laser to stop immediately, so that damage due to a broken or fractured fiber will be minimized.

What is claimed is:

1. In conjunction with a laser which produces laser energy directed into an optical fiber delivery system, a device for detecting a break or fracture in the optical fiber delivery system, comprising infrared detector means for receiving infrared emissions from the optical fiber delivery system and for generating a temperature signal in response thereto, means for discriminating a portion of the temperature signal due to infrared emissions of a break or fracture in the optical fiber delivery system from the remainder of said temperature signal, means for comparing said portion of said temperature signal to a threshold level and generating a reset signal when said portion of said temperature signal exceeds said threshold level, and means for receiving said reset signal and stopping further operation of the laser system.

2. In conjunction with a laser which produces a plurality of pulses of laser energy directed into an optical fiber delivery system, a device for detecting a break or fracture in the optical fiber delivery system, comprising infrared detector means for receiving infrared emissions from the optical fiber delivery system and for generating a temperature signal in response thereto, means for discriminating a portion of the temperature signal due to infrared emissions of a break or fracture in the optical fiber delivery system from the remainder of said temperature signal, means for comparing said portion of said temperature signal to a threshold level and generating a reset signal when said portion of said temperature signal exceeds said threshold level, and means for receiving said reset signal and stopping further operation of the laser system.

3. The device of claim 2, wherein said means for discriminating includes gating means interposed between said infrared detector means and said means for comparing, said gating means receiving said temperature signal and conducting said temperature signal only during a brief interval each laser pulse is extinguished.

4. The device of claim 3, wherein said means for comparing includes a fist operational amplifier having one input connected to said temperature signal and the other input connected to a voltage reference source.

5. The device of claim 4, wherein said infrared detector means includes an infrared sensor connected across the inputs of a second operational amplifier.

6. The device of claim 5, wherein said gating means includes timer means for receiving a laser firing control pulse and for generating a timer output pulse in response thereto, said timer output pulse having a predetermined delay with respect to the cessation of said laser firing control pulse.

7. The device of claim 6, wherein said gating means further includes a solid state switch including means for actuating said switch with said timer output pulse.

* * * * *